US011768146B2

(12) United States Patent
Kimura et al.

(10) Patent No.: US 11,768,146 B2
(45) Date of Patent: Sep. 26, 2023

(54) FINE PARTICLE MEASUREMENT DEVICE

(71) Applicant: Sumitomo Electric Industries, Ltd., Osaka (JP)

(72) Inventors: Akinori Kimura, Osaka (JP); Asako Motomura, Osaka (JP); Yoko Sugiyama, Osaka (JP); Hiroshi Suganuma, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 234 days.

(21) Appl. No.: 17/023,566

(22) Filed: Sep. 17, 2020

(65) Prior Publication Data

US 2021/0003494 A1 Jan. 7, 2021

Related U.S. Application Data

(63) Continuation of application No. PCT/JP2019/010936, filed on Mar. 15, 2019.

(30) Foreign Application Priority Data

Mar. 20, 2018 (JP) ................................ 2018-052953

(51) Int. Cl.
*G01N 15/14* (2006.01)
*G01N 15/00* (2006.01)

(52) U.S. Cl.
CPC . *G01N 15/1434* (2013.01); *G01N 2015/0023* (2013.01); *G01N 2015/144* (2013.01)

(58) Field of Classification Search
CPC ............. G01N 15/14334; G01N 15/06; G01N 2015/0023; G01N 2015/149
USPC .................. 356/246, 432–440, 335–343, 73; 422/68.1, 82.05
See application file for complete search history.

(56) References Cited

U.S. PATENT DOCUMENTS

| | | | | |
|---|---|---|---|---|
| 5,074,662 | A * | 12/1991 | Sullivan | G01N 21/03 356/244 |
| 6,184,990 | B1 | 2/2001 | Amirkhanian et al. | |
| 6,603,535 | B1 * | 8/2003 | McDowell | G01P 5/001 356/28 |
| 2006/0232780 | A1 * | 10/2006 | King | G01N 15/1459 356/436 |

(Continued)

FOREIGN PATENT DOCUMENTS

| | | |
|---|---|---|
| EP | 0 950 890 A2 | 4/1999 |
| JP | H07-035679 A | 2/1995 |

(Continued)

*Primary Examiner* — Hoa Q Pham
(74) *Attorney, Agent, or Firm* — McCarter & English, LLP; Michael A. Sartori

(57) ABSTRACT

A fine particle measurement device includes a support stand (20) that has a groove (F) extending in a predetermined direction and is configured to support in the groove an observation container (10), which has an elongate shape and accommodates a liquid sample containing a fine particle therein such that an extending direction of the groove (F) coincides with a longitudinal direction of the observation container (10); and an imaging unit (40) that is configured to capture an image of the fine particle in the observation container (10) at a position where the support stand is out of a field of view, the observation container (10) being supported by the support stand (20).

6 Claims, 21 Drawing Sheets

(56) References Cited

U.S. PATENT DOCUMENTS

| | | | |
|---|---|---|---|
| 2016/0370342 | A1 | 12/2016 | Kimura et al. |
| 2017/0345148 | A1 | 11/2017 | Tomoda et al. |
| 2018/0202921 | A1 | 7/2018 | Kobayashi |
| 2020/0096435 | A1 | 3/2020 | Kimura et al. |

FOREIGN PATENT DOCUMENTS

| | | | |
|---|---|---|---|
| JP | H10-073528 | A | 3/1998 |
| JP | 2001-221736 | A | 8/2001 |
| JP | 2004-532405 | A | 10/2004 |
| JP | 2009-183469 | A | 8/2009 |
| JP | 2009-537826 | A | 10/2009 |
| JP | 2013-255437 | A | 12/2013 |
| JP | 2014-517263 | A | 7/2014 |
| JP | 2017-044939 | A | 3/2017 |
| WO | 02/080090 | A1 | 10/2002 |
| WO | 2007/137119 | A2 | 11/2007 |
| WO | 2012/142496 | A1 | 10/2012 |
| WO | 2018/221430 | A1 | 12/2018 |

* cited by examiner (A)

(B)

(A)

(B)

(A)

(B)

(A)

(B)

(A)

(B)

FINE PARTICLE MEASUREMENT DEVICE

This application is a continuation application of PCT/JP2019/010936 claiming the benefit of priority of the Japanese Patent Application No. 2018-052953, filed on Mar. 20, 2018, the entire contents of which are incorporated herein by reference.

TECHNICAL FIELD

The present disclosure relates to a fine particle measurement device.

BACKGROUND ART

Various methods for acquiring an image of a fine particle such as a cell to evaluate the three-dimensional shape of the fine particle have been studied (for example, Patent Literatures 1 and 2 and the like).

CITATION LIST

Patent Literature

Patent Literature 1: Japanese Unexamined Patent Publication No. 2014-517263

Patent Literature 2: Japanese Unexamined Patent Publication No. 2004-532405

SUMMARY OF INVENTION

Solution to Problem

A fine particle measurement device of the present disclosure includes a support stand that has a groove extending in a predetermined direction and is configured to support in the groove an observation container, which has an elongate shape and accommodates a liquid sample containing a fine particle therein such that an extending direction of the groove coincides with a longitudinal direction of the observation container; and an imaging unit that is configured to capture an image of the fine particle in the observation container at a position where the support stand is out of a field of view, the observation container being supported by the support stand.

DESCRIPTION OF EMBODIMENTS

Description of Embodiments of Present Invention

Figure 1:
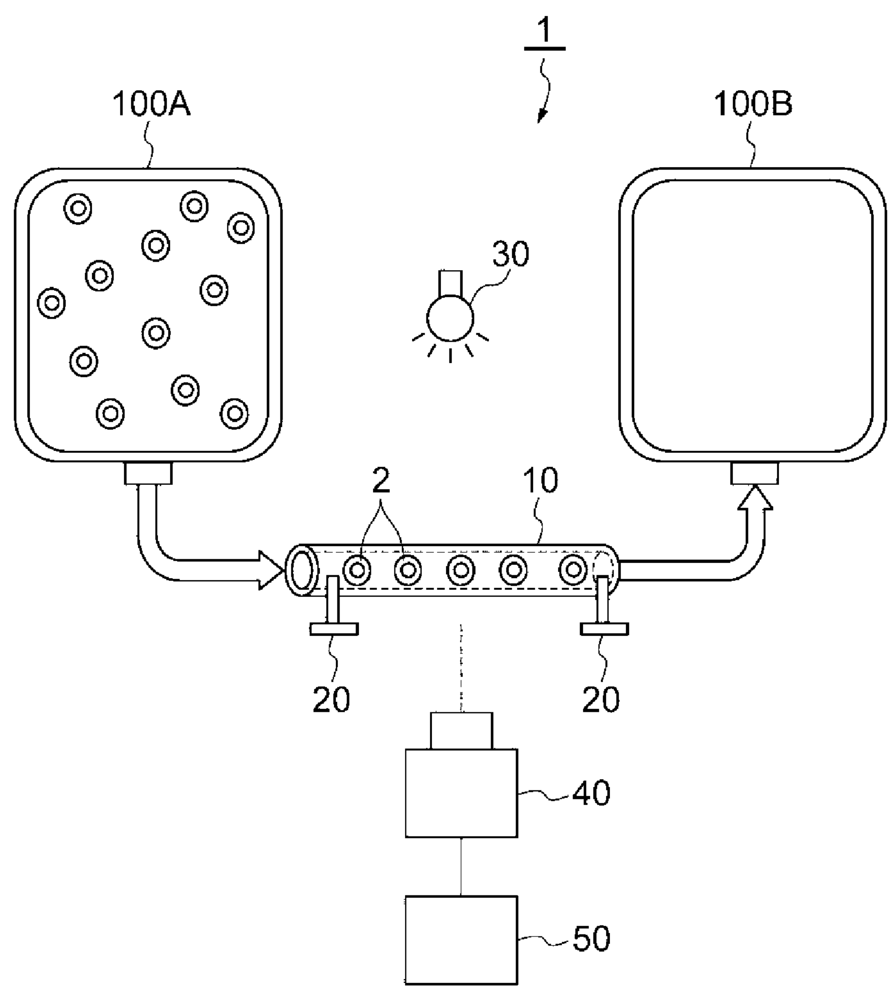
FIG. 1 is a schematic configuration view illustrating a state where an observation container is arranged in a fine particle measurement device of the present disclosure.

First, embodiments of a fine particle measurement device of the present disclosure will be listed and described.

(1) According to the present disclosure, there is provided a fine particle measurement device including: a support stand that has a groove extending in a predetermined direction and is configured to support in the groove an observation container, which has an elongate shape and accommodates a liquid sample containing a fine particle therein such that an extending direction of the groove coincides with a longitudinal direction of the observation container; and an imaging unit that is configured to capture an image of the fine particle in the observation container at a position where the support stand is out of a field of view, the observation container being supported by the support stand.

According to the fine particle measurement device, the observation container is accommodated in the groove of the support stand, and thus the observation container can be supported such that the extending direction of the groove coincides with the longitudinal direction of the observation container. In this state, since the imaging unit is configured to capture an image of the fine particle at the position where the support stand is out of the field of view, the image of the fine particle can be captured in a state where the observation container is properly supported, and thus the image of the shape of the fine particle can be more accurately captured.

(2) In addition, the groove of the support stand may have a V shape.

Since the groove has a V shape, regardless of the shape of a bottom portion of the observation container, the observation container can be accommodated in and suitably supported by the groove.

(3) In addition, a pressing jig that is configured to press the observation container supported by the support stand may be further provided.

Since the pressing jig that is configured to press the observation container is further provided, a movement of the observation container on the support stand can be restricted, so that an image of the fine particle can be more suitably captured.

(4) A movement mechanism that is configured to move the support stand, the observation container, or the imaging unit may be further provided.

Since the movement mechanism that is configured to move the support stand, the observation container, or the imaging unit is provided, the field of view of the imaging unit can be easily changed, so that an image of the fine particle in the observation container can be more simply captured.

(5) A light source unit that is configured to irradiate the observation container with light may be further provided.

Since the light source unit is provided, for example, an image of fluorescent light that the fine particle emits in response to light from the light source unit can be captured, and thus when the imaging unit captures the image, a wider range of information on the fine particle can be obtained.

(6) An outer packaging in which the support stand and the imaging unit are installed may be further provided.

Since the outer packaging in which the support stand and the imaging unit are installed is provided, the fine particle measurement device can be easily moved, so that the versatility is improved.

(7) Transporting means for transporting the outer packaging may be further provided.

When the transporting means for transporting the outer packaging is provided, the fine particle measurement device can be more simply transported.

DETAILED DESCRIPTION OF EMBODIMENTS OF PRESENT INVENTION

Hereinafter, specific examples of a fine particle measurement device according to the present disclosure will be described with reference to the drawings. Incidentally, it is intended that the present disclosure is not limited to the examples provided and includes all modifications within the concept and the scope implied by the claims and equivalent to the claims.

In recent years, with the development of the regenerative medicine or the like, a technique for mass-culturing a cell using a culture bag or the like has been studied. Therefore, there is increasing needs for a device that performs a measurement on a fine particle such as the cell cultured in the culture bag or the like. However, in a configuration of the device that has been studied in the related art, when the cell is observed, the focal position may not be properly adjustable.

(Fine Particle Measurement Device)

FIG. 1 is a schematic configuration view illustrating a state where an observation container is arranged in a fine particle measurement device according to one embodiment of the present disclosure. As illustrated in FIG. 1, a fine particle measurement device 1 is a device that performs a measurement on fine particles that are dispersed in a sample. The fine particles and a target in which the fine particles are dispersed are not particularly limited, and may be, for example, a liquid. As an example where the fine particles are dispersed in a liquid sample, the fine particles may be cells and the liquid where the fine particles are dispersed may be a cell culture medium, an aqueous solution such as a physiological saline solution which is suitable for the cells, water, or the like. In addition, examples of cells which are targets include a spheroid, an egg, a mini organ, and the like. Incidentally, in the present embodiment, an example where the sample is a liquid sample and the fine particles are dispersed in a liquid will be described; however, as long as the sample may contain the fine articles that are imaging targets, the present disclosure is not limited to the configuration where the fine particles are dispersed in the liquid.

As illustrated in FIG. 1, when a liquid sample containing a fine particle that is an object 2 stays in an observation container 10 for measurement, the fine particle measurement device 1 detects light from the object 2, which is obtained by irradiating the object 2 in the observation container 10 with measurement light, to capture a transmission image and to perform a measurement, an analysis, and the like on the object 2 based on the transmission image. For this reason, the fine particle measurement device 1 includes a support stand 20 that supports the observation container 10, a light source unit 30, an imaging unit 40, and an analyzer 50. Incidentally, examples of the light from the object 2 include transmitted light, diffuse reflected light, fluorescent light, and the like from the object 2, which are induced by the light source unit 30 (or light from other light sources). Namely, an optical measurement technique for the object 2 by the light source unit 30 and the imaging unit 40 is not particularly limited.

Figure 2:
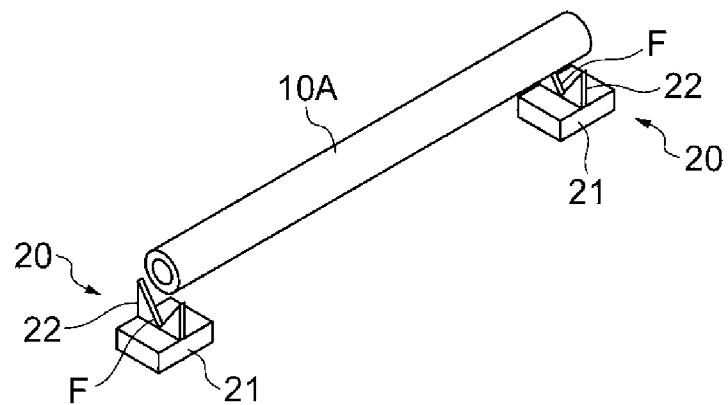
FIG. 2 is a view illustrating a specific configuration example of a support stand of the fine particle measurement device of the present disclosure, where region (A) illustrates an example where an observation container having a cylindrical shape is placed and region (B) illustrates an example where an observation container having a square tube shape is placed.
Figure 2:
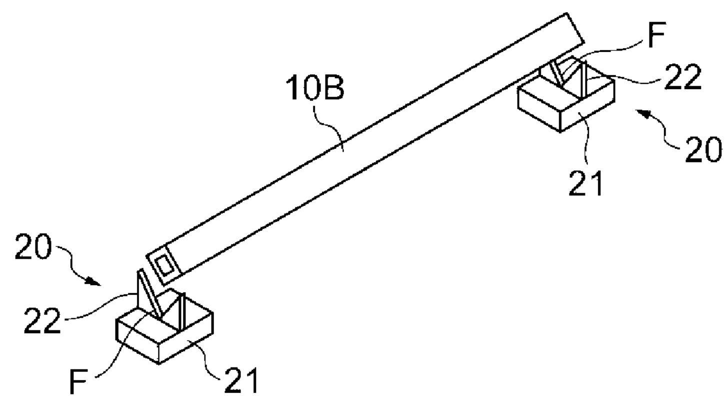

The observation container 10 is a container that accommodates the liquid sample containing a fine particle when a measurement is performed on the fine particle. In addition, the support stand 20 supports the observation container 10, for example, on a measurement stand. FIG. 2 illustrates a specific configuration example of the observation container 10 and the support stand 20.

As illustrated in FIG. 2, the observation container 10 (10A and 10B) may have, for example, a cylindrical shape with both open ends. Region (A) of FIG. 2 illustrates an observation container 10A having a cylindrical shape. In addition, region (B) of FIG. 2 illustrates an observation container 10B having a square tube shape. As illustrated in FIG. 1, culture bags 100A and 100B are connected to both ends of the observation container 10 having a cylindrical shape, and while the liquid sample containing the fine particle that is the object 2 is moved from one culture bag 100A to the other culture bag 100B, an observation can be performed.

When the observation container 10 has a square tube shape, the cross-sectional shape may have a rectangular or square form. Namely, the shape may have right-angled corners. The three-dimensional shape of the object 2 can be suitably measured by such a shape or elaborating on an arrangement of the imaging unit 40.

The size of the observation container 10 is not particularly limited, and is appropriately set according to an arrangement of the light source unit 30 and the imaging unit 40, the size of the fine particle that is the object 2, and the like. In addition, the material of the observation container 10 is not particularly limited, and for example, glass, PC resin, PS resin, or the like can be used. At least a region of the observation container 10 through which light incident into the imaging unit 40 passes, namely, a region of the observation container 10 which is arranged in an imaging region of the imaging unit 40 is required to have transparency for the measurement light. In addition, the observation container 10 may be configured to have a uniform thickness (cross-section thickness) in the region of the observation container 10, the region being arranged in the imaging region of the imaging unit 40. When the thickness of the observation container 10 is not uniform, since light from the imaging region is refracted to be incident into the imaging unit 40, the imaging unit 40 may acquire a distorted image of the object 2. Since the thickness of the above region of the observation container 10 is uniform, the imaging unit 40 can capture a transmission image which is prevented from being affected by distortion when the measurement light or light from the object 2 passes through the observation container 10.

The support stand 20 supports the observation container 10 having a cylindrical shape in a predetermined direction. For this reason, the support stand 20 includes a base portion 21 and a container support portion 22 in the upper surface (side opposite a base portion 21 side) of which a groove F extending in one direction is formed. The base portion 21 may have, for example, a plate shape. In addition, the container support portion 22 is made of a plate-shaped member that is provided on one main surface of the base portion 21 to extend upward from the main surface. Then, an end portion of the plate-shaped member may be processed to provide the groove F extending in a thickness direction the plate-shape member forming the container support portion 22, so that the container support portion 22 is produced. Incidentally, the support stand 20 illustrated in region (A) and region (B) of FIG. 2 is provided with a V-shaped groove (V groove), which can accommodate the observation container 10A or the observation container 10A, as the groove F. The length of the groove F (thickness of the container support portion 22) may be, for example, approximately 0.5 mm to 50 mm. When the groove F having a V shape is provided, the angle formed by two surfaces forming the V shape may be approximately 60° to 120°. When the angle formed by the two surfaces of the groove F is 90°, the observation container 10B having right-angled corners can be suitably held. However, the shape of the groove F is not limited to the above V shape. In addition, the shape of the groove F can be appropriately changed according to the shape, the size, or the like of the observation container 10 accommodating the groove F.

The light source unit 30 irradiates a predetermined region (for example, the vicinity of the center) of the observation container 10 with the measurement light. A halogen lamp, an LED, or the like can be used as a light source of the light source unit 30. In addition, the light source unit 30 may have a function of modulating the intensity.

As illustrated in FIG. 1, the light source unit 30 may be configured to be arranged to correspond to the imaging unit 40 to irradiate the observation container 10 with light. With such an arrangement, a measurement by the imaging unit 40 can be more accurately performed. In addition, the imaging unit 40 is arranged in a state where the support stand 20 is out of the field of view. With such a configuration, the imaging unit 40 can suitably capture an image of the object 2 in the observation container 10 while avoiding interference with the support stand 20.

Incidentally, in the present embodiment, visible light or near infrared light can be used as the measurement light irradiated by the light source unit 30 in order to observe the transmitted light or the diffuse reflected light. The visible light or the near infrared light is light of which the wavelength range is included in a wavelength band (band A) of 400 nm to 2,000 nm. In addition, light included in a wavelength band (band B) of 300 nm to 800 nm which is used to excite the fluorescent light can be also used as the measurement light irradiated by the light source unit 30 in order to observe the fluorescent light. In addition, a combination of light included in the band A and light included in the band B may be the measurement light.

The imaging unit 40 has a function of receiving light, which of the measurement light irradiated from the light source unit 30 transmits through the object 2, to detect the intensity of the light. Namely, the imaging unit 40 is provided at a position to face the light source unit 30 with the observation container 10 interposed therebetween. The imaging unit 40 includes a detector in which a plurality of pixels are two-dimensionally arranged, and converts light, which is received by the pixels, into intensity information. A detection result of the imaging unit 40 is sent to the analyzer 50.

The imaging unit 40 may be configured to detect, for example, only the intensity of light of a specific wavelength by which the object 2 can be distinguished from other components. In addition, the imaging unit 40 may be configured to detect a spectroscopic spectrum including intensity values for a plurality of wavelengths. The spectroscopic spectrum is a series of data where intensity values at random wavelengths extracted from spectral information are paired with the corresponding wavelengths.

For example, a CMOS, a CCD, an InGaAs detector, a mercury cadmium tellurium (MCT) detector, or the like can be used as the detector of the imaging unit 40. In addition, when the imaging unit 40 is configured to detect a spectroscopic spectrum, the imaging unit 40 further includes a spectroscope, which has a function of dispersing incident light for each wavelength, in a front stage of the detector. For example, a wavelength selective filter, an interference optical system, a diffraction grating, or a prism can be used as the spectroscope.

In addition, the imaging unit 40 may be a hyperspectral sensor that acquires a hyperspectral image. The hyperspectral image is an image in which one pixel is formed of N wavelength data, and includes spectral information including intensity data where a plurality of wavelengths correspond to each pixel. Namely, the hyperspectral image is three-dimensionally configured data having both of two-dimensional elements as an image and elements as spectral data because of the feature that each of the pixels forming the image has intensity data of a plurality of wavelengths. Incidentally, in the present embodiment, the hyperspectral image is an image formed of pixels having intensity data in at least four wavelength bands per pixel.

Incidentally, a case where light from in the imaging unit 40, the object 2 is dispersed and then a spectroscopic spectrum is acquired has been described above; however, the configuration when a spectroscopic spectrum is acquired in the imaging unit 40 is not limited to the above configuration. For example, a configuration where the wavelength of light emitted from the light source unit 30 is variable may be adopted.

The analyzer 50 has a function of acquiring an imaging result related to the object 2 sent from the imaging unit 40 and performing arithmetic processing and the like to display and record the image of the object 2 and perform a measurement, an analysis, or the like on the image. In addition, the analyzer 50 may be configured to perform various calculations and the like based on a measurement result and the like. For example, when the objects 2 are cells, a configuration where the diameters of the objects 2 of which the images are captured are calculated and a distribution, a histogram, or the like of the diameters is displayed may be adopted. In addition, a configuration where the objects 2 included in the image are counted in number to calculate the concentration of the objects 2 contained in the liquid sample may be adopted.

Next, an arrangement of the light source unit 30 and the imaging unit 40 will be described with reference to FIGS. 3, 4A, 4B, and 4C.

Figure 3:
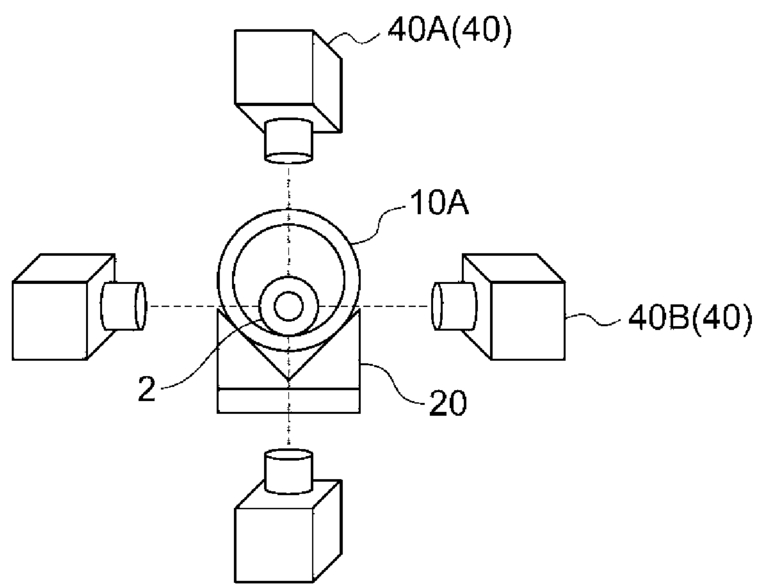
FIG. 3 is a view describing an arrangement of an imaging unit with respect to the observation container having a tube shape, where region (A) illustrates the case of the observation container having a cylindrical shape and region (B) illustrates the case of the observation container having a square tube shape.
Figure 3:
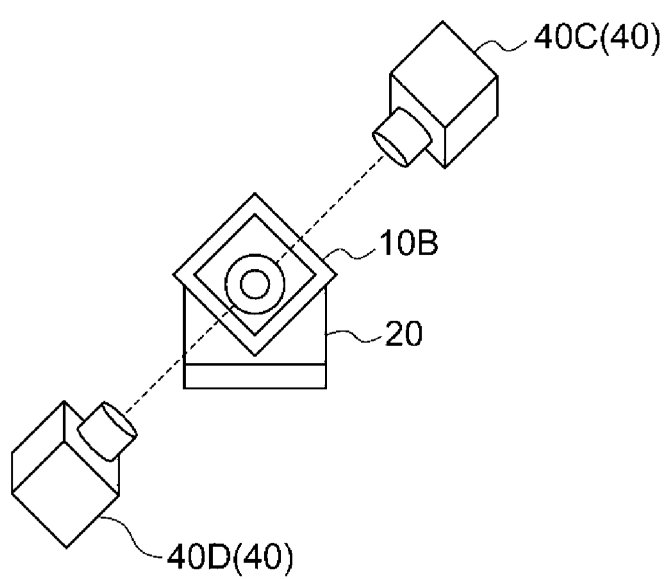

Region (A) of FIG. 3 illustrates an example of an arrangement of the imaging unit 40 with respect to the observation container 10A having a cylindrical shape. Region (A) of FIG. 3 illustrates the observation container 10A on the support stand 20, and the support stand 20 is arranged at a position out of the field of view of the imaging unit 40. This point is the same also for region (B) of FIG. 3.

When the observation container 10A has a cylindrical shape, an arrangement of the imaging unit 40 is not particularly limited, and the imaging unit 40 may be arranged at a position to suitably capture an image of the object 2. Therefore, as illustrated in region (A) of FIG. 3, an arrangement of the imaging unit 40 with respect to the observation container 10A and the object 2 can be appropriately changed. However, the imaging unit 40 may be configured to be arranged at a position where an optical axis of light which passes through a wall surface of the observation container 10A to be incident into the imaging unit 40 is orthogonal to the wall surface of the container. With such a configuration, the imaging unit 40 can be prevented from receiving reflected light, refracted light, or the like from the wall surface of the container.

In addition, a configuration where a plurality of the imaging units 40 are provided may be adopted. In that case, as illustrated with imaging units 40A and 40B in region (A) of FIG. 3, the plurality of imaging units 40 may be arranged in positions where optical axes are orthogonal to each other around the object 2. With such a configuration, an image of the shape of the fine particle that is the object 2 can be suitably captured by the imaging units 40A and 40B.

In addition, the imaging units 40A and 40B may be configured to capture an image of the same imaging target at the same time. With such a configuration, one imaging target (object 2) in the observation container 10A can be identified from different directions. The object 2 can be considered to rotate as the liquid sample moves. Therefore, the imaging units 40A and 40B are configured to capture an image of the observation container 10A in a specific position, and thus more detailed information on the object 2 can be acquired. Incidentally, the expression "that an image of the same imaging target is captured at the same time" refers to that as seen along a longitudinal direction of the observation container 10, the positions of the fields of view of the imaging units 40A and 40B are the same and an image of the object 2 staying at a certain point in the observation container 10 is captured at the same time.

Region (B) of FIG. 3 illustrates an example of an arrangement of the imaging unit 40 when the observation container 10B has a square tube shape. When the observation container 10B has a square tube shape, the imaging unit 40 may be configured to be arranged at a position where an optical axis of light which passes through a wall surface of the observation container 10B to be incident into the imaging unit 40 is orthogonal to the wall surface of the container. With such a configuration, the imaging unit 40 can be prevented from receiving reflected light, refracted light, or the like from the wall surface of the container. Specifically, the imaging unit 40 may be arranged to face the wall surface that is flat and included in the observation container 10B having a square tube shape.

In addition, when a plurality of the imaging units are provided, as illustrated in region (B) of FIG. 3, imaging units 40C and 40D may be arranged to face each other while interposing the observation container 10B having a square tube shape therebetween. When the imaging units 40C and 40D are in such an arrangement and are configured to capture an image of the same imaging target at the same time, the imaging units 40C and 40D can capture the entire image of the object in the observation container 10B.

Figure 4A:
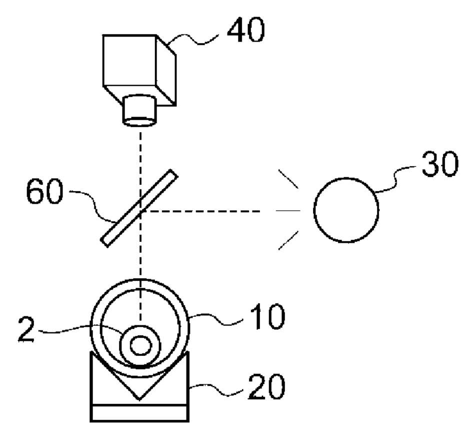
FIG. 4A is a view describing an arrangement of the observation container, and a light source unit and the imaging unit of the fine particle measurement device of the present disclosure.
Figure 4B:
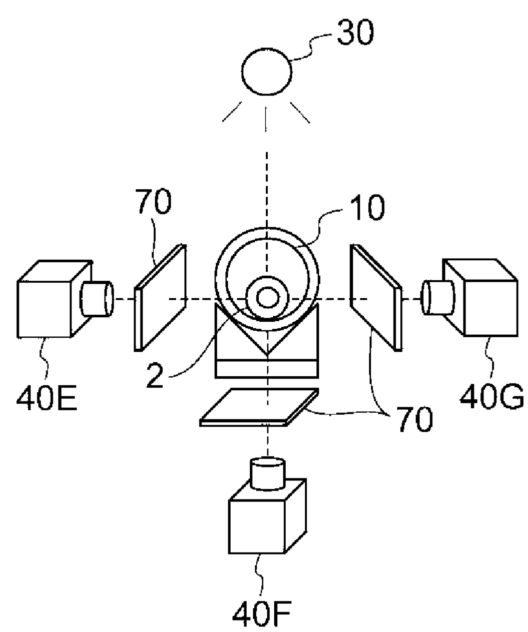
FIG. 4B is a view describing another arrangement of the observation container, and the light source unit and the imaging unit of the fine particle measurement device of the present disclosure.
Figure 4C:
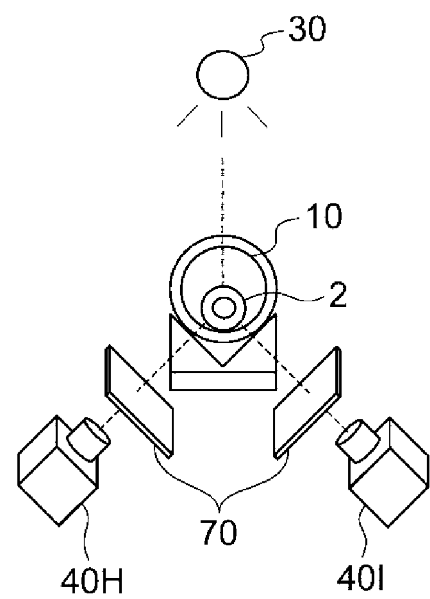
FIG. 4C is a view describing further another arrangement of the observation container, and the light source unit and the imaging unit of the fine particle measurement device of the present disclosure.

FIGS. 4A, 4B, and 4C illustrates examples of an arrangement of the light source unit 30 and the imaging unit 40. FIG. 1 describes a case where the light source unit 30 and the imaging unit 40 face each other while interposing the observation container 10 therebetween, and a positional relationship between the light source unit 30 and the imaging unit 40 can be appropriately changed. For example, an example illustrated in FIG. 4A has an configuration where a half-silvered mirror 60 is provided, light from the light source unit 30 is reflected by the half-silvered mirror 60 to irradiate the object 2, and the light from the object 2 transmits through the half-silvered mirror 60 to be incident into the imaging unit 40. As described above, a configuration using an optical element or the like that changes the path of light may be adopted.

In addition, in an example illustrated in FIG. 4B, three imaging units 40 (40E to 40G) are provided for one light source unit 30. Among the three imaging units 40, an imaging unit 40F is arranged to face the light source unit 30 with the observation container 10 (object 2) interposed therebetween. Imaging units 40E and 40G are arranged at positions where optical axes of light incident into the imaging units are at 90° with respect to an optical axis of light from the light source unit 30 toward the object 2. When the object 2 emits fluorescent light for the light (excitation light) from the light source unit 30 and the fluorescent light is observed by the imaging units 40E to 40G, as a filter 70 that restricts light of a specific wavelength toward the imaging unit 40, a filter that blocks light of the specific wavelength including the excitation light may be provided in a front stage of each of the imaging units 40. Incidentally, even if the fluorescent light from the object 2 is not observed, a filter that blocks light of a specific wavelength may be provided as the filter 70.

In addition, in an example illustrated in FIG. 4C, two imaging units 40 (40H and 40I) are provided for one light source unit 30. Two imaging units 40H and 40I are arranged at positions where optical axes of light incident into the imaging units are at 60° with respect to an optical axis of light from the light source unit 30 toward the object 2. For this reason, the imaging units 40H and 40I can capture an image of reflected light from the object 2 or an image of fluorescent light when the object 2 emits the fluorescent light. In addition, the filter 70 that restricts the wavelength of light incident into each of the imaging units 40 is arranged in the front stage of each of the imaging units 40.

As illustrated in FIGS. 4B and 4C, as described above, the numbers of the light source units 30 and the imaging units 40 may differ from each other. In addition, the transmitted wavelengths of the filters 70 provided in the front stages of the plurality of imaging units 40 may differ from each other.

(Modification Example Related to Supporting Observation Container)

Next, a modification example of a support configuration of the observation container 10 will be described. As described above, the observation container 10 is accommodated in the groove F of the support stand 20 and supported by the support stand 20, and a pressing jig can be used as means that restricts a movement of the observation container 10 on the support stand 20.

Figure 5:
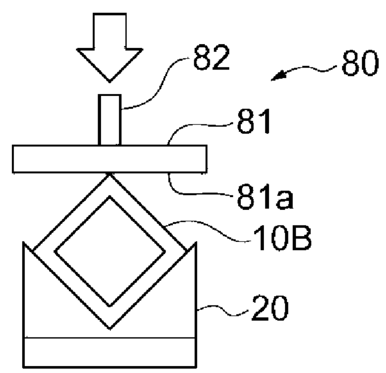
FIG. 5 is a view describing a pressing jig of the fine particle measurement device of the present disclosure, where region (A) illustrates an example where the observation container having a square tube shape is pressed and region (B) illustrates an example where the observation container having a cylindrical shape is pressed.
Figure 5:
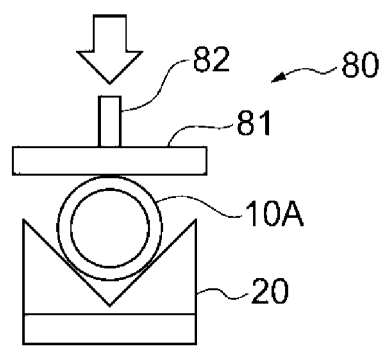

FIG. 5 illustrates an example of a pressing jig 80. The pressing jig 80 includes a pressing portion 81 having a pressing surface 81*a* to be pressed against the observation container 10 and a holding portion 82 that a user of the pressing jig 80 holds when handling the pressing portion 81.

Region (A) of FIG. 5 illustrates a state where the observation container 10B having a square tube shape is accommodated in the groove F of the support stand 20 and the observation container 10B is supported from above by the pressing jig 80. In addition, region (B) of FIG. 5 illustrates a state where the observation container 10A having a cylindrical shape is accommodated in the groove F of the support stand 20 and the observation container 10B is supported from above by the pressing jig 80. In both of the examples, since the observation container 10 is supported from above by the pressing jig 80, a movement of the observation container 10 on the groove F can be restricted.

Figure 6:
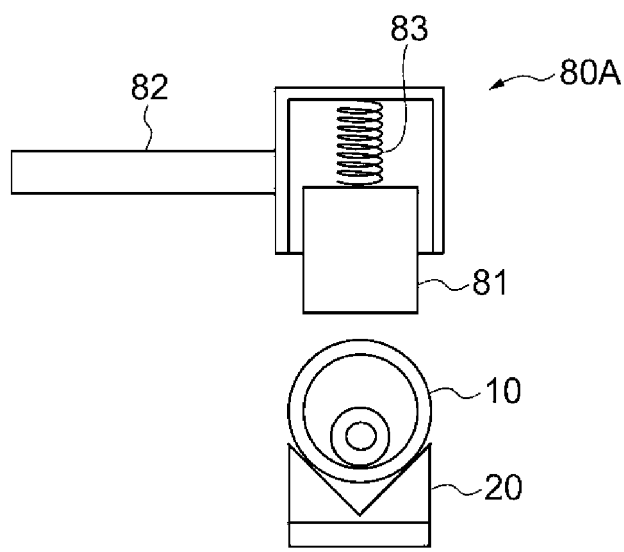
FIG. 6 is a view describing a modification example of the pressing jig, where region (A) illustrates a state where the observation container is not pressed and region (B) illustrates a state where the observation container is pressed.
Figure 6:
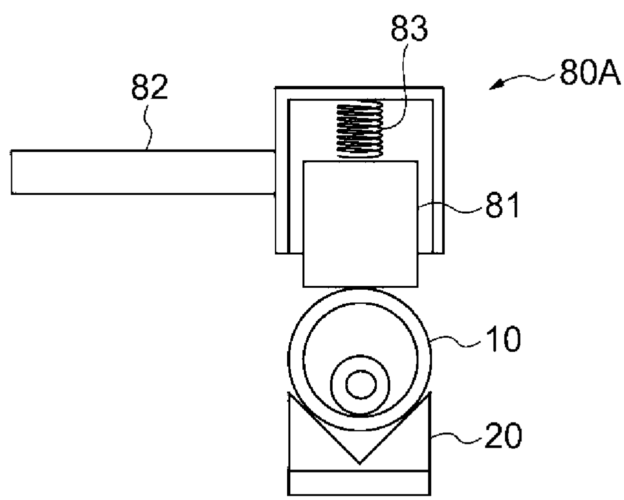

Furthermore, when the shape of the pressing jig 80 is changed, the function of supporting the observation container 10 can be improved. For example, in a pressing jig 80A illustrated in FIG. 6, the pressing portion 81 is connected to the holding portion 82 via a spring 83. As illustrated in region (A) of FIG. 6, in a state where the observation container 10 is not pressed, the pressing portion 81 of the pressing jig 80A is connected to the holding portion 82 via the spring 83. On the other hand, as illustrated in region (B) of FIG. 6, in a state where the observation container 10 is pressed (supported), the pressing portion 81 of the pressing jig 80A is pressed and supported from above via the holding portion 82 and the spring 83. With such a configuration, since a force from the holding portion 82 can be more gently transmitted to the pressing portion 81 than when the pressing portion 81 is directly pressed and supported by the holding portion 82, for example, the rotation of the observation container 10 or the like can be prevented from causing the force from the holding portion 82 to act to move the observation container 10 from the support stand 20.

Figure 7:
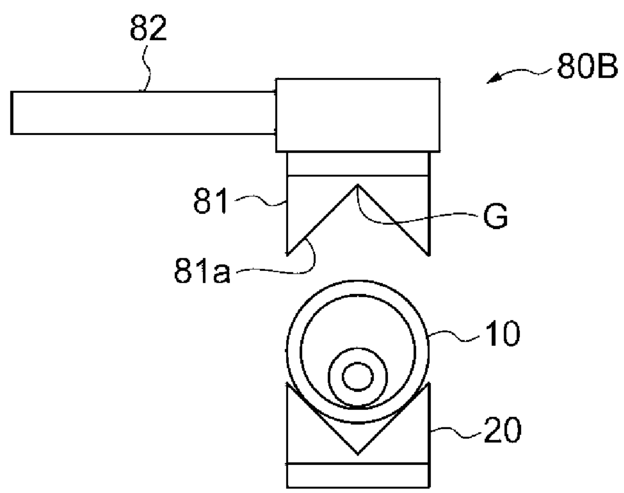
FIG. 7 is a view describing a further modification example of the pressing jig, where region (A) illustrates a state where the observation container is not pressed and region (B) illustrates a state where the observation container is pressed.
Figure 7:
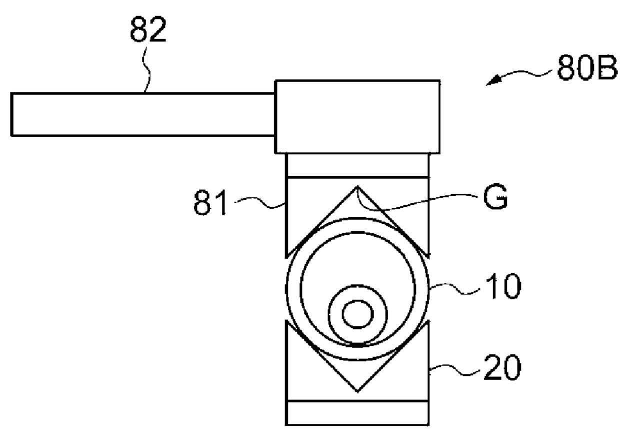

In a pressing jig 80B illustrated in FIG. 7, a groove G is formed in the pressing surface 81*a* of the pressing portion 81. In this case, when a transition is made from a state in which the observation container 10 is not pressed and which is illustrated in region (A) of FIG. 7 to a state in which the observation container 10 is pressed (supported) and which is illustrated in region (B) of FIG. 7, since the observation container 10 is accommodated in the groove G of the pressing surface 81*a*, a movement of the observation container 10 can be suitably restricted. Incidentally, in order to restrict a movement of the observation container 10 as described above, the pressing jig 80B is used in such a manner that the longitudinal direction of the observation container 10 (extending direction of the groove F of the support stand 20) coincides with an extending direction of the groove G in the pressing surface 81*a* of the pressing jig 80B.

Figure 8A:
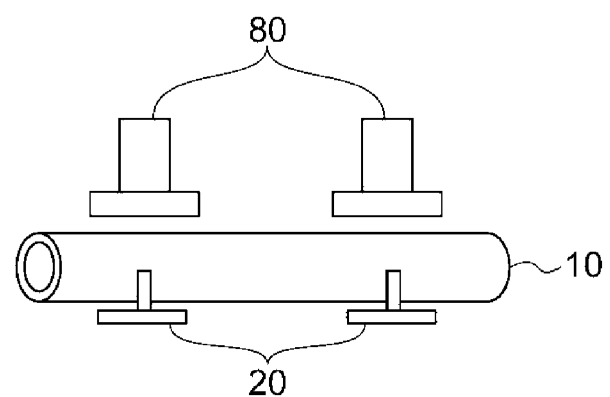
FIG. 8A is a view describing a positional relationship between the support stand and the pressing jig.
Figure 8B:
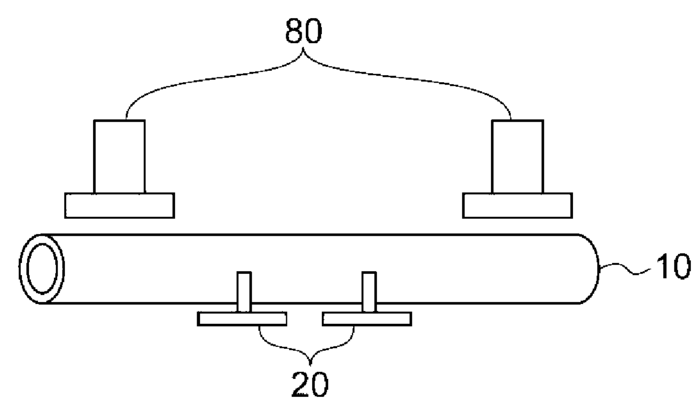
FIG. 8B is a view describing a positional relationship between the support stand and the pressing jig.
Figure 8C:
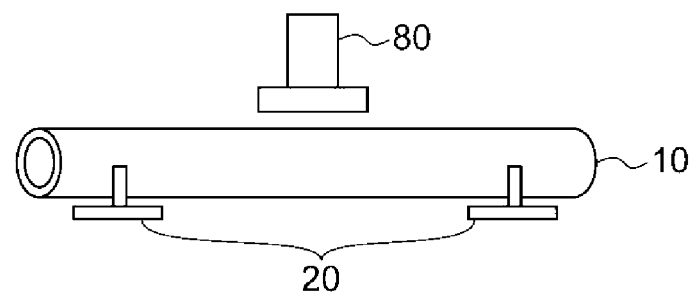
FIG. 8C is a view describing a positional relationship between the support stand and the pressing jig.

Incidentally, a positional relationship between the support stand 20 for the observation container 10 and the pressing jig 80 is not particularly limited. FIGS. 8A, 8B, and 8C are views illustrating examples of the positional relationship between the support stand 20 and the pressing jig 80. FIG. 8A illustrates a state where the support stand 20 and the pressing jig 80 are arranged to face each other with the observation container 10 interposed therebetween. In addition, FIG. 8B illustrates a state where two support stands 20 support a central side in the longitudinal direction of the observation container 10, whereas two pressing jigs 80 support end portion sides in the longitudinal direction of the observation container 10. In addition, FIG. 8C illustrates a state where two support stands 20 support end portion sides in the longitudinal direction of the observation container 10, whereas one pressing jig 80 supports the vicinity of the center in the longitudinal direction of the observation container 10. As described above, the numbers of the support stands 20 and the pressing jigs 80 and the positional relationship therebetween can be appropriately changed.

Incidentally, both of the support stand 20 and the pressing jig 80 may be configured to be provided at positions out of the field of view of the imaging unit 40. Therefore, as illustrated in FIG. 8C, when the pressing jig 80 is arranged in the vicinity of the center of the observation container 10, the imaging unit 40 may be arranged between the support stand 20 and the pressing jig 80 along the longitudinal direction of the observation container 10.

(Application Example of Fine Particle Measurement Device)

An application example of the fine particle measurement device described above will be described with reference to FIG. 9. In an example illustrated in FIG. 9, similarly to FIG. 1, the culture bag is connected to the observation container 10 placed in the fine particle measurement device 1. However, when compared to the example illustrated in FIG. 1, the point of coincidence is that the culture bag 100A is connected to one (upstream side) end portion, and the point of difference is that two culture bags 100B and 100C are connected to the other (downstream side) end portion and a branch portion 110 connected to a flow path to the culture bag 100B and a flow path to the culture bag 100C is connected to a rear stage of the observation container 10.

Figure 9:
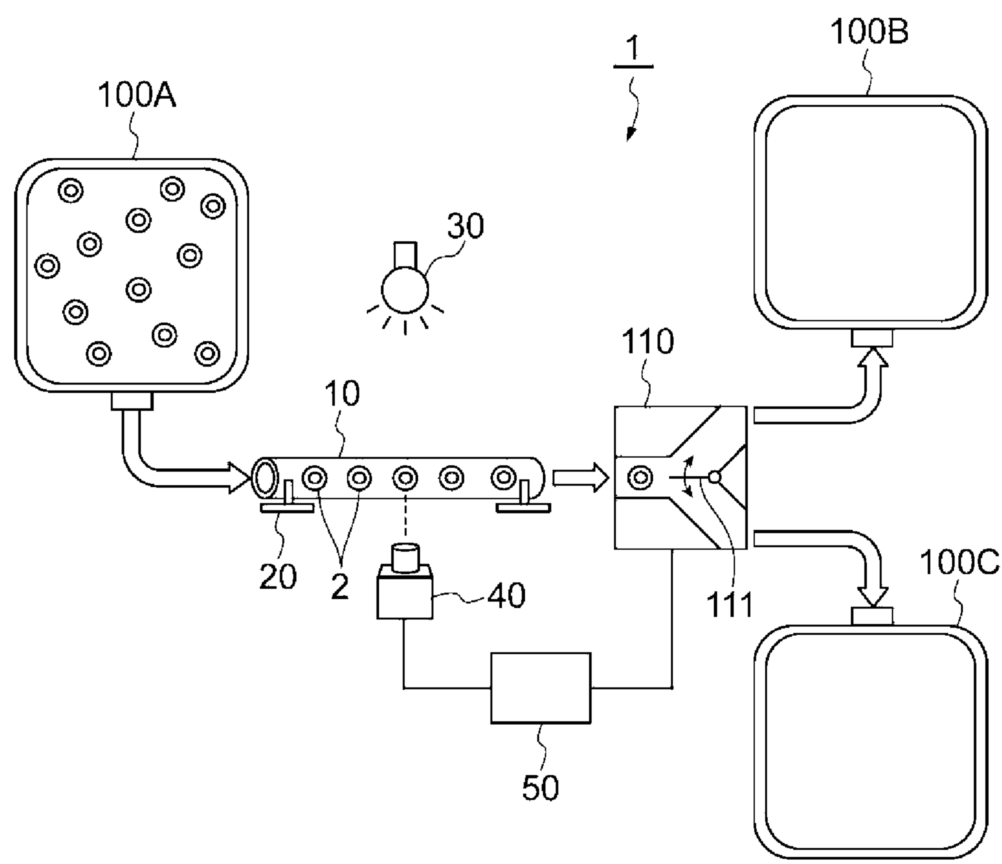
FIG. 9 is a view describing an application example of the fine particle measurement device.

In the example illustrated in FIG. 9, while the liquid sample containing the objects 2 is moved from the culture bag 100A toward the observation container 10, the imaging unit 40 captures images of the objects 2 and the analyzer 50 performs an analysis on the objects 2. Then, a valve 111 provided in the branch portion 110 is controlled according to the result to cause the objects 2 to move to either of the culture bag 100B and the culture bag 100C.

As in the example illustrated in FIG. 9, a configuration where the objects 2 are sorted by using analysis results obtained by the fine particle measurement device 1 may be adopted. For example, the objects 2 having diameters exceeding a predetermined diameter may be moved to the culture bag 100B, and the other objects 2 may be moved to the culture bag 100C. Incidentally, the way the objects 2 are sorted by using the analysis results can be appropriately changed. In addition, a configuration where only the objects 2 satisfying a specific condition are recovered and the other objects 2 are discarded may be adopted. In addition, the configuration of the branch portion 110 that sorts the fine particles can be appropriately changed.

(Modification Example of Observation Container)

Next, a modification example of the observation container 10 will be described.

FIGS. 1 and 2 and the like describe a case where the observation container 10 has a cylindrical shape and the culture bags 100A and 100B and the like are connected to both ends thereof; however, the observation container may be a recessed container and may have a structure where the liquid sample is contained therein. In addition, the observation container may have a structure where a plurality of recessed portions are provided to individually accommodate the objects 2.

Figure 10A:
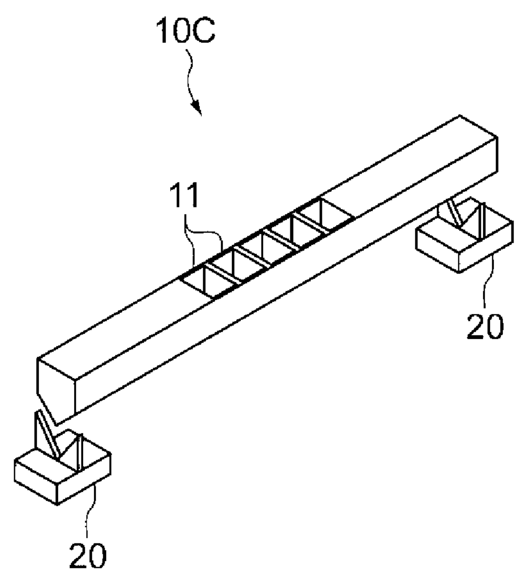
FIG. 10A is a perspective view illustrating a modification example of the observation container together with the support stand.

For example, as a structure where the observation container is provided with the plurality of recessed portions, it can be considered that the observation container 10 is made of an elongated columnar member and the plurality of recessed portions are provided in the vicinity of the center thereof. In such a shape, a region of the observation container (for example, an end portion of the observation container), in which the recessed portion is not formed, can be supported by the support stand 20. FIG. 10A is a perspective view illustrating an observation container 10C according to the modification example together with the support stand. The observation container 10C has a structure where a plurality of recessed portions 11 are independent of each other as described above. In addition, the observation container 10C is an elongated columnar member and the plurality of recessed portions 11 are formed in the vicinity of the center thereof. A region of the observation container 10C (for example, an end portion of the observation container 10C), in which the recessed portion 11 is not formed, can be supported by the support stand 20.

Figure 10B:
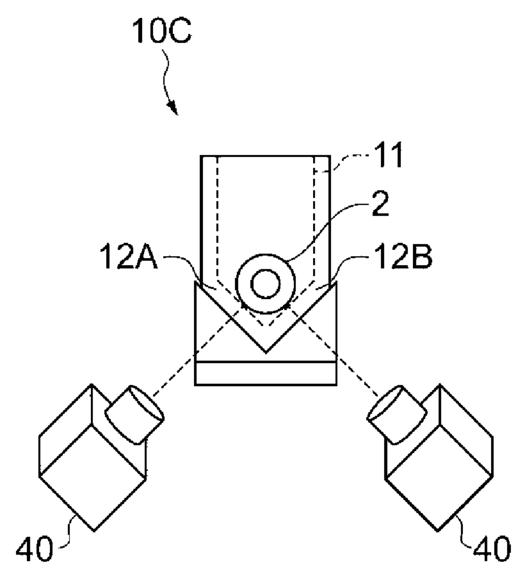
FIG. 10B is a conceptual view illustrating one example of a cross section of the observation container of FIG. 10A and an arrangement of the imaging unit.

In addition, when the observation container 10 is provided with the plurality of recessed portions, the recessed portion may be configured such that two bottom walls made of two plate-shaped members are combined to form a bottom surface having a corner. FIG. 10B is a conceptual view illustrating one example of the cross section of the observation container 10C and an arrangement of the imaging unit, and illustrates an example where the recessed portion 11 is formed of bottom walls 12A and 12B made of two plate-shaped members. The angle formed by the two bottom walls 12A and 12B is not particularly limited, but may be approximately 90° or in a range of 90°±30°. With such a configuration, two imaging units 40 can use the two bottom walls 12A and 12B to suitably obtain an image used to three-dimensionally identify the shape of the fine particle that is the object 2. Particularly, when the bottom walls 12A and 12B are arranged to be orthogonal to each other, the imaging units can suitably capture an image of the shape of the fine particle that is the object 2.

In addition, as with the observation container 10C, in the configuration where the plurality of recessed portions 11 are independently provided, for example, the recessed portions 11 different from each other may be configured to accommodate the object 2 one by one. With such a configuration, a plurality of the objects 2 can be prevented from being falsely observed and a movement of each of the objects 2 is also restricted, and thus an analysis on the object 2 can be suitably performed.

Incidentally, instead that the plurality of recessed portions 11 are provided, similarly to the observation container 10, the observation container 10C may be configured such that one recessed portion 11 extending in the longitudinal direction is provided. In addition, the shape of the bottom wall of the observation container 10 can be appropriately changed.

Figure 11A:
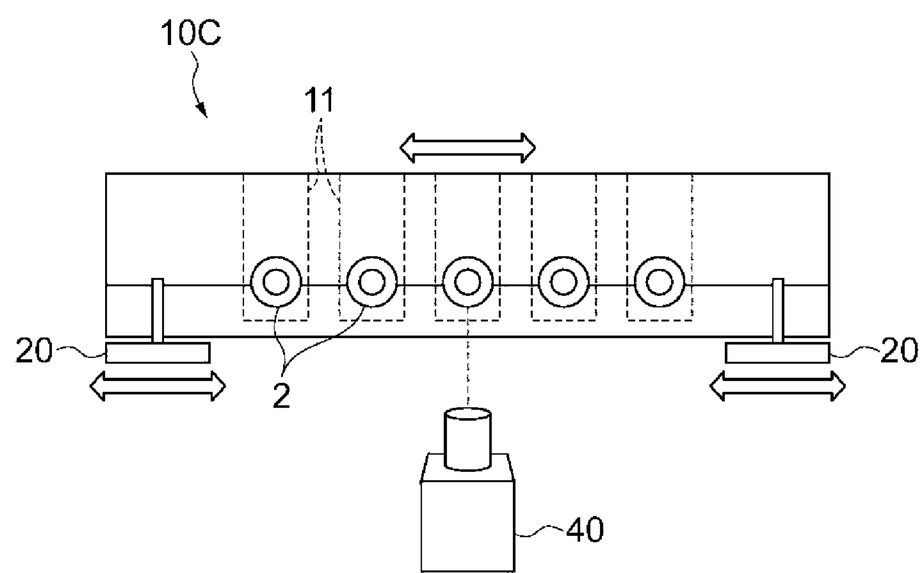
FIG. 11A is a view describing a movement mechanism.

As with the observation container 10C described above, in a case where the shape of the observation container 10 is not a cylindrical shape and is provided with the recessed portion 11, when the object 2 in the container is observed, the imaging unit 40 or the observation container 10 is required to be moved. Therefore, as illustrated in FIG. 11A, the observation container 10C on the support stand 20 or the imaging unit 40 may be configured to be moved along an extending direction (longitudinal direction) of the observation container 10C, so that the object (recessed portion in which the object 2 is accommodated) in the field of view of the imaging unit 40 is changed. Specifically, the fine particle measurement device 1 may be configured such that a movement mechanism which moves the observation container 10C or a movement mechanism which moves the imaging unit 40 is provided. Incidentally, as the movement mechanism that moves the observation container 10C, the observation container 10C itself may be moved or the support stand 20 may be moved to be able to move the support stand 20 and the observation container 10C at the same time.

Figure 11B:
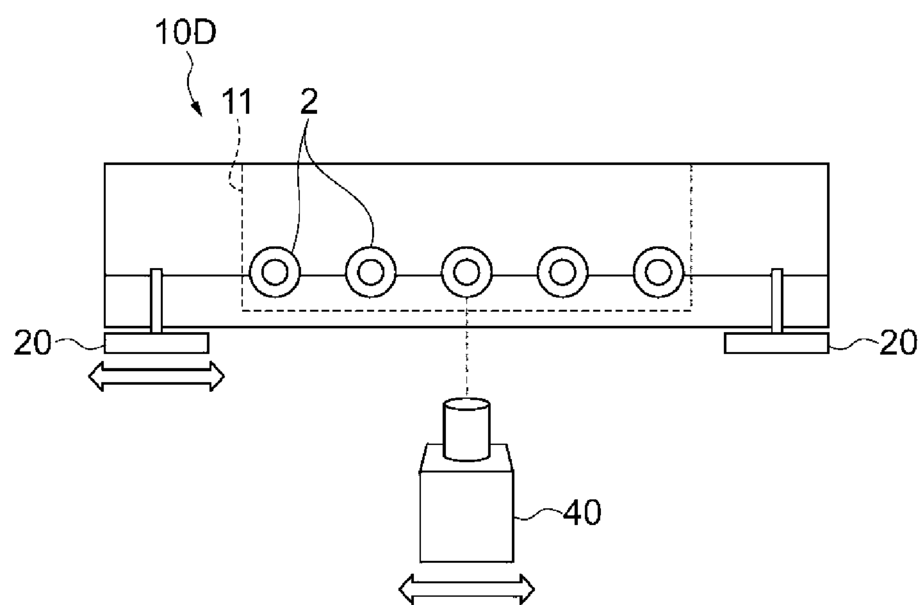
FIG. 11B is a view describing a movement mechanism.

In addition, as illustrated in FIG. 11B, also in a case where an observation container 10D is provided with one recessed portion, when the recessed portion extends in the longitudinal direction and a plurality of the objects are accommodated in the one recessed portion, similarly to the configuration of FIG. 11A, the fine particle measurement device 1 may be configured such that a movement mechanism which moves the observation container 10D or a movement mechanism which moves the imaging unit 40 is provided. Incidentally, also when the observation container 10D is made of a cylindrical member, the fine particle measurement device 1 may be configured to include a movement mechanism.

(Modification Example of Support Stand)

Figure 12:
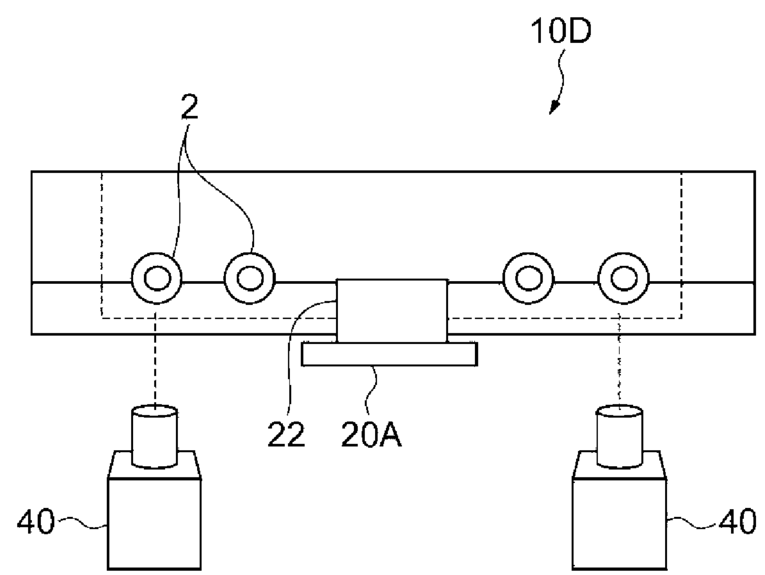
FIG. 12 is a view describing a modification example of the support stand.

In the above embodiments, an example where one observation container 10 is supported by two support stands 20 has been described; however, the number or shape of the support stands 20 that support the observation container 10 can be appropriately changed. For example, a configuration where one observation container 10 is supported by three support stands 20 may be adopted. In addition, as illustrated in FIG. 12, a configuration where one observation container 10 (here, representing the observation container 10D) is supported by one support stand 20 may be adopted. In a support stand 20A illustrated in FIG. 12, the thickness (length along the extending direction of the observation container 10D) of the container support portion 22 of the support stand 20A is larger than that of the support stand 20 illustrated in FIGS. 1 and 2 and the like. For this reason, a long length of the groove F formed along the thickness direction can be secured, and the observation container 10D can be stably supported by the groove F of the container support portion 22. Therefore, even if the number of the support stands 20 is reduced, the observation container 10 (10D) can be suitably supported. Incidentally, as illustrated in FIG. 12, when the support stand 20 is provided in the vicinity of the center of the observation container 10D, the imaging unit 40 can be arranged at a position where the support stand 20 is out of the field of view (for example, on an end portion side of the observation container). With such a configuration, the object 2 can be suitably observed.

(Modification Example of Fine Particle Measurement Device)

Figure 13A:
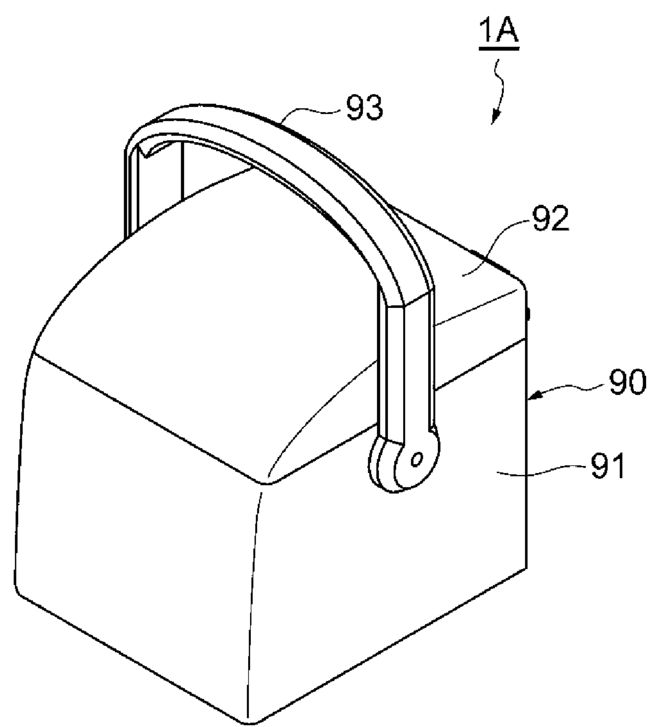
FIG. 13A is a perspective view illustrating a state where a lid portion of the fine particle measurement device of the present disclosure is closed.
Figure 13B:
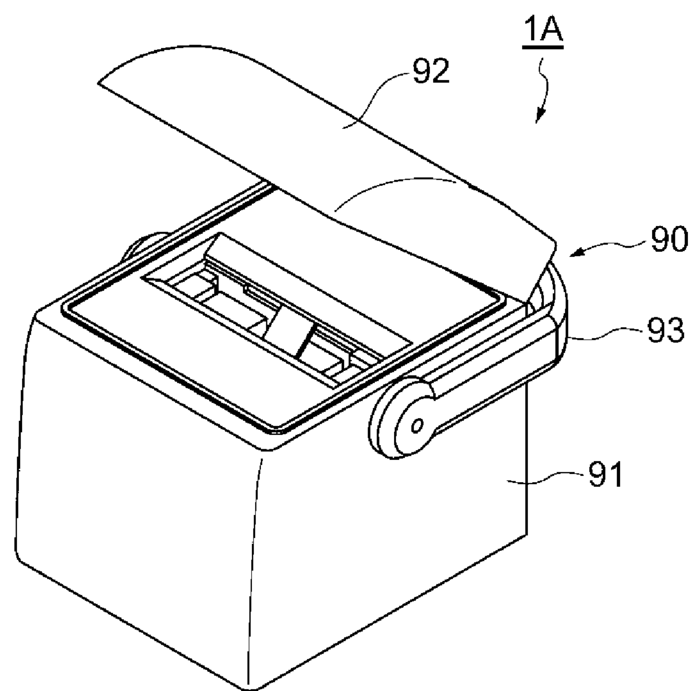
FIG. 13B is a perspective view illustrating a state where the lid portion of the fine particle measurement device of the present disclosure is opened.
Figure 14:
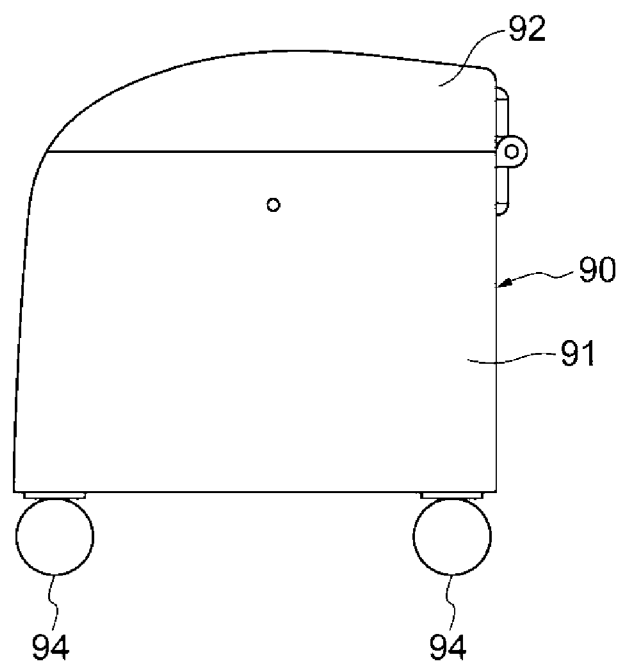
FIG. 14 is a perspective view illustrating another example of the fine particle measurement device of the present disclosure.

FIGS. 13A, 13B, and 14 illustrate modification examples of the fine particle measurement device. FIG. 13A is a perspective view illustrating a state where a lid portion 92 of a fine particle measurement device 1A is closed, and FIG. 13B is a perspective view illustrating a state where the lid portion 92 of the fine particle measurement device 1A is opened. In the fine particle measurement device 1A, the support stand 20, the light source unit 30, and the imaging unit 40 are installed in an outer packaging 90 for transport. The outer packaging 90 includes a main body portion 91 and the lid portion 92, and as transporting means for transporting the outer packaging 90, a handle 93 is attached to the main body portion 91. During transport of the fine particle measurement device 1A, the observation container 10, the support stand 20, the light source unit 30, and the imaging unit 40 are installed in the outer packaging 90. As illustrated in FIG. 13A, during transport, the lid portion 92 is closed and the handle 93 can be used to carry the fine particle measurement device 1. In addition, during usage, as illustrated in FIG. 13B, the lid portion 92 is opened, the observation container 10 is set on the support stand 20 in the outer packaging 90, and a measurement is performed. As described above, since the support stand 20, the light source unit 30, and the imaging unit 40 are configured to be installed in the outer packaging 90, the fine particle measurement device 1A can be transported to any place to be used, so that the versatility of the fine particle measurement device 1A is improved.

Incidentally, as illustrated in FIG. 14, as the transporting means, instead of the handle 93, a caster 94 may be configured to be provided in the main body portion 91, so that the fine particle measurement device 1A can be transported. The position where the caster 94 is provided can be appropriately changed.

As described above, in the fine particle measurement device 1 according to the present embodiment, the observation container 10 is accommodated in the groove F of the support stand 20, and thus the observation container 10 can be supported such that the extending direction of the groove F coincides with the longitudinal direction. In this state, since the imaging unit 40 is configured to capture an image of the fine particle at the position where the support stand 20 is out of the field of view, the image of the fine particle can be captured in a state where the observation container 10 is properly supported, and thus the image of the shape of the fine particle can be more accurately captured.

Since the groove F of the support stand 20 has a V shape, regardless of the shape of a bottom portion of the observation container 10, the observation container 10 can be accommodated in and suitably supported by the groove F.

In addition, since the pressing jig 80 that is configured to press the observation container 10 is further provided, a movement of the observation container 10 on the support stand 20 can be restricted, so that an image of the fine particle can be more suitably captured.

In addition, since the movement mechanism that is configured to move the support stand 20, the observation container 10, or the imaging unit 40 is provided, the field of view of the imaging unit 40 can be easily changed, so that an image of the fine particle in the observation container 10 can be more simply captured.

In addition, since the light source unit 30 is provided, for example, an image of fluorescent light that the fine particle emits in response to light from the light source unit 30 can be captured, and thus when the imaging unit 40 captures the image, a wider range of information on the fine particle can be obtained. Incidentally, even if the light source unit 30 is not provided, for example, the fine particle can be observed; however, since the light source unit 30 is provided, an observation using light of a specific wavelength can be suitably performed.

In addition, as with the fine particle measurement device 1A, since the outer packaging 90 in which the support stand 20, the light source unit 30, and the imaging unit 40 are installed is provided, the fine particle measurement device can be easily moved, so that the versatility is improved.

Furthermore, when the transporting means for transporting the outer packaging 90 is provided, the fine particle measurement device can be more simply transported.

Incidentally, the fine particle measurement device 1 according to the present disclosure is not limited to the above embodiments. For example, instead of the configuration where the fine particle measurement device 1 includes the observation container 10, the support stand 20, the light source unit 30, the imaging unit 40, and the analyzer 50 as in the above embodiments, for example, a configuration where the light source unit is not provided may be adopted. In addition, the number of the light source units or the imaging units may be 3 or more. In addition, the observation container 10 may not be included in the fine particle measurement device.

In addition, the shape of the observation container 10 can be appropriately changed. The object 2 may be able to stay at least in the observation container 10. Therefore, as with the observation containers 10A and 10B, a configuration where the liquid sample containing the object 2 is accommodated through an opening connected to the outside may be adopted, or as with the observation containers 10C and 10D, a configuration where one or a plurality of the recessed portions 11 are provided may be adopted.

REFERENCE SIGNS LIST

1, 1A: fine particle measurement device, 10: observation container, 11: recessed portion, 20: support stand, 30: light source unit, 40: imaging unit, 50: analyzer, 80: pressing jig, 90: outer packaging.

The invention claimed is:

1. A fine particle measurement device comprising:

a support stand that has a groove extending in a predetermined direction and is configured to support in the groove an observation container, which has an elongate shape and accommodates a liquid sample containing a fine particle therein, such that an extending direction of the groove coincides with a longitudinal direction of the observation container; and a plurality of imaging units each configured to capture an image of the fine particle in the observation container at a position where the support stand is out of a field of view, the observation container being supported by the support stand, wherein the observation container has two bottom walls made of two plate-shaped members, which are combined to form a bottom surface having a corner, and wherein the image units are configured to capture images of the same imaging target at the same time, so that one imaging target in the observation container can be identified from different directions.

2. The fine particle measurement device according to claim 1, wherein the groove of the support stand has a V shape.

3. The fine particle measurement device according to claim 1, further comprising:

an outer packaging in which the support stand and the imaging units are installed.

4. The fine particle measurement device according to claim 1, wherein each of the imaging units includes a detector in which a plurality of pixels are two-dimensionally arranged, the detector converting light received by the pixels to intensity information.

5. The fine particle measurement device according to claim 1, wherein each of the imaging units includes at least one of a CMOS, a CCD, an InGaAs detector, a mercury cadmium tellurium (MCT) detector, and a hyperspectral sensor.

6. The fine particle measurement device according to claim 1, wherein the plurality of imaging units include three or more imaging units.

* * * * *